(12) United States Patent
Heuser

(10) Patent No.: US 6,536,949 B1
(45) Date of Patent: Mar. 25, 2003

(54) CATHETER FOR THERMAL EVALUATION OF ARTERIOSCLEROTIC PLAQUE

(76) Inventor: Richard R. Heuser, 2626 E. Arizona Biltmore Cir., No. 9, Phoenix, AZ (US) 85016

( * ) Notice: Subject to any disclaimer, the term of this patent is extended or adjusted under 35 U.S.C. 154(b) by 0 days.

(21) Appl. No.: 09/521,091

(22) Filed: Mar. 7, 2000

(51) Int. Cl.⁷ .............................. G01K 7/02; A61B 5/01
(52) U.S. Cl. ...................... 374/179; 600/549; 600/372; 600/381
(58) Field of Search ................................ 374/147, 148, 374/179, 208; 600/549, 372, 373, 377, 380, 381; 136/221

(56) References Cited

U.S. PATENT DOCUMENTS

| | | | |
|---|---|---|---|
| 2,729,211 A | * | 1/1956 | Peter .......................... 600/373 |
| 3,751,305 A | * | 8/1973 | Huebscher .................. 374/208 |
| 4,241,289 A | * | 12/1980 | Bowling ...................... 136/221 |
| 4,590,669 A | * | 5/1986 | Imamura ..................... 374/208 |
| 4,796,640 A | * | 1/1989 | Webler ........................ 600/549 |
| 5,176,144 A | * | 1/1993 | Yoshikoshi et al. ......... 600/549 |
| 5,207,228 A | * | 5/1993 | Roelandt et al. ............ 600/549 |
| 5,213,417 A | * | 5/1993 | Yamada et al. ............. 374/208 |
| 5,217,019 A | * | 6/1993 | Hughes ....................... 600/549 |
| 5,275,488 A | * | 1/1994 | Stelts ........................ 374/208 |
| 5,281,793 A | * | 1/1994 | Gavin et al. ................. 374/208 |
| 5,356,486 A | * | 10/1994 | Sugarman et al. .......... 374/208 |
| 5,364,392 A | | 11/1994 | Warner et al. |
| 5,370,459 A | * | 12/1994 | Culbertson et al. ......... 374/208 |
| 5,462,359 A | * | 10/1995 | Reichl et al. ................ 374/148 |
| 5,545,193 A | * | 8/1996 | Fleischman et al. ........ 600/373 |
| 5,578,008 A | | 11/1996 | Hara |
| 5,660,473 A | * | 8/1997 | Noma et al. ................ 374/208 |
| 5,688,266 A | * | 11/1997 | Edwards et al. ............ 600/549 |
| 5,725,524 A | * | 3/1998 | Mulier et al. ............... 600/373 |
| 5,733,044 A | * | 3/1998 | Rose et al. .................. 374/148 |
| 5,743,900 A | | 4/1998 | Hara |
| 5,769,077 A | * | 6/1998 | Lindegren ................... 600/373 |
| 5,792,070 A | * | 8/1998 | Kauphusman et al. ...... 600/549 |
| 5,853,409 A | * | 12/1998 | Swanson et al. ............ 600/549 |
| 5,906,636 A | | 5/1999 | Casscells, III et al. |
| 5,935,075 A | | 8/1999 | Casscells et al. |
| 5,938,694 A | * | 8/1999 | Jaraczewski et al. ....... 600/373 |
| 5,957,961 A | * | 9/1999 | Maguire et al. ............ 600/549 |
| 5,997,526 A | * | 12/1999 | Giba et al. .................. 600/373 |
| 6,064,902 A | * | 5/2000 | Haissaguerre et al. ...... 600/381 |

FOREIGN PATENT DOCUMENTS

| | | | | |
|---|---|---|---|---|
| JP | 03094773 | * | 4/1991 | ................ 600/549 |
| JP | 3073999902 | | 9/1999 | |

OTHER PUBLICATIONS

Berkenboom, Guy. "Unstable arterosclerotic plaque, Pathophysiology and therapeutic guidlines." *Acta Cardiologica*. vol. 53, No. 4, 1998: 235–241.

(List continued on next page.)

*Primary Examiner*—Diego Gutierrez
*Assistant Examiner*—Madeline Gonzalez
(74) *Attorney, Agent, or Firm*—Kolisch Hartwell, P.C.

(57) ABSTRACT

A device for percutaneous insertion into a fluid passageway of a human body, such as an artery is provided with one or more thermocouples disposed on a flexible, resilient wire lead and coupled to a temperature monitor. The wire lead includes a distal portion formed in a single, oval, looped shape or a double, ovoid or basket-like, looped shape with the thermocouples disposed on a side or tip of the shape. The wire lead is configured, e.g., by insertion in a guidewire, for slidable movement through the artery to an area of interest, e.g., at a buildup of arteriosclerotic plaque, on an inner surface of the artery, to bring the thermocouple into resiliently biased contact with the inner surface at the area of interest for measurement of the temperature there.

20 Claims, 1 Drawing Sheet

OTHER PUBLICATIONS

Casscells, Ward, et al. "Thermal detection of cellular infiltrates in living atherosclerotic plaques: possible implications for plaque rupture and thrombosis." *The Lancet*. vol. 347, May 25, 1996: 1447–1449.

Depre, Christophe, et al. "Pathology of Unstable Plaque: Correlation With the Clinical Severity of Acute Coronary Syndromes." *JAAC*. vol..30, No.3, Sep. 1997: 694–702.

Kristensen, Steen Dalby, et al. "Insights Into the Pathophysiology of Unstable Coronary Artery Disease." *The American Journal of Cardiology*. vol 80 (5A), Sep. 4, 1997: 5E–9E.

Lauer, Micheal A, et al. "The Temperature of Atherosclerotic Lesions in Hypercholesterolemic Rabbit Double Injury Model are Elevated Following Angioplasty." *JACC* Feb. 1999: 67A.

Pasterkamp, Gerard, et al. "Inflammation of the Atherosclerotic Cap and Shoulder of the Plaque Is a Common and Locally Observed Feature in Unruptured Plaques of Femoral and Coronary Arteries." *Arterioscler Thromb Vasc Biology*. Jan. 1999: 54–58.*

Ravn, Berg Hanne and Erling Falk. "Histopathology of Plaque Rupture." *Cardiology Clinics*. vol. 17, No. 2, May 1999: 263–270.*

Ridker, P.M. "Inflammation, artherosclerosis, and cardiovascular risk: an epidemiologic view." *Blood Coagulation and Fibrinolysis* vol. 10 (suppl 1), 1999: S9–S12.*

Shah, Prediman K. "Plaque Disruption and Coronary Thrombosis: New Insight into Pathogenesis and Prevention," *Clinical Cardiology*. vol. 20 (Suppl. II), 1997: II–38–II–44.*

Stefandis, Christodoulos, et al. "Thermal Heterogeneity Within Human Atherosclerotic Coronary Arteries Detected In Vivo, A New Method of Detection by Application of a Special Thermography Catheter." *Circulation*. Apr. 20, 1999: 1695.*

Willerson, James T. "Stable Angina Pectoris: Recent Advances in Predicting Prognosis and Treatment," *Advances in Internal Medicine*. vol. 43, 1998: 175–202.*

"Thermography identifies plaque vulnerability." *Non–invasive Imaging*, Sep. 1999: 29.*

* cited by examiner

CATHETER FOR THERMAL EVALUATION OF ARTERIOSCLEROTIC PLAQUE

BACKGROUND

This invention relates generally to an apparatus and method for remotely measuring temperature within a passageway, particularly along an interior surface of the passageway. More particularly the invention concerns an apparatus and method for measuring temperature within a human fluid passageway, e.g., a major artery, and determining temperature variations at and around arteriosclerotic plaque within the passageway.

Coronary heart disease takes two forms, a chronic form and an acute form, the latter being the more dangerous because it involves a buildup of unstable plaque within an artery. The unstable plaque is prone to rupture, which often leads to activation of clotting factors in the bloodstream and formation of a blood clot, possibly resulting in a stroke or myocardial infarction. Furthermore, in acute coronary heart disease, sudden death is the first warning sign in up to 25% of cases. Therefore, clinical trials have been conducted to develop a way to diagnose acute coronary heart disease by assessing the nature of the plaque buildup. The trials have indicated that the amount of plaque, the degree of blood vessel narrowing, and the appearance of the plaque under angiography are not helpful in determining the vulnerability of the plaque to rupture. Thus, new ways to identify and manage dangerous vulnerable plaques could add much to the prevention and treatment of life-threatening acute coronary events.

Stable plaques, called atheromas, have thick fibrous caps, smaller lipid cores, and are less likely to rupture. Unstable plaques, on the other hand, are characterized by thin fibrous caps, weakness in the blood vessel wall, and increased inflammatory cells. Angiography and intravascular ultrasound can be used to detect the presence and size of plaque within coronary vessels. These invasive techniques, however, cannot determine the stability and composition of the plaques. Angioscopy, an invasive technique that has shown promise in its ability to detect disruptions in blood vessel linings, is no longer available in the United States. Such invasive techniques carry significant risks and require large bore catheters to accomplish which produce trauma to delicate blood vessels.

Recent investigations have examined plaque temperature as an indicator of plaque instability. Casscells et al. examined blood vessels with plaques taken from human patients who had undergone carotid endarterectomy. Using a thermistor probe with a needle tip, these researchers demonstrated that plaque temperatures varied from 0.5-degrees to 3-degrees C. across the surface of the carotid artery plaques. They concluded that temperature variance was related to the accumulation of macrophages, i.e., inflammatory cells, beneath the plaque cap, with higher temperatures associated with greater macrophage buildup.

Stefanadis et al. measured temperature of plaques using a thermography catheter inserted through a guiding catheter within the coronary vessels. Temperature measurements were taken at five locations near five different vessel lesion sites. Their findings indicate that arteriosclerotic plaques showed greater surface temperatures, with the highest temperatures and greatest variation in temperatures present for patients with unstable angina and myocardial infarction.

SUMMARY OF THE INVENTION

The invented device and method provides for measuring temperature within a human fluid passageway, particularly on an inner surface of the passageway in an area of arteriosclerotic plaque, with a minimum degree of risk to delicate blood vessel linings and at a minimum cost for the device. According to the invention, a thermocouple is disposed on a flexible, resilient, and very fine wire lead at a distal portion of the lead, and the lead is inserted through a guidewire with the distal portion of the wire lead extending from a distal end of the guidewire, and the guidewire is inserted percutaneously into the fluid passageway.

The distal portion of the wire lead is formed in an oval, looped or basket shape, having a tip and two or more sides with the thermocouple disposed on one of the sides at a point of maximum outer circumference for the oval shape, and/or on the tip. As the distal portion of the wire lead is slidably moved through the passageway through portions of the passageway having an inner circumference less than the outer circumference of the oval shape, the shape flexes resiliently, biasing the thermocouple against the inner surface of the passageway. Thus, the thermocouple is in direct, biased contact with the inner surface for accurate measurement of the surface temperature, with minimum danger of damage to the blood vessel lining.

The thermocouple at the tip of the looped shape is useful to measure the temperature at areas of near-total or total occlusion where the lead cannot pass and, in areas with less plaque, to measure the temperature in the bloodstream adjacent to the plaque surface. The distal portion of the wire lead may also be formed in an L-shape with the thermocouple disposed at the tip of the L.

DETAILED DESCRIPTION OF THE PREFERRED EMBODIMENTS

Figure 1:
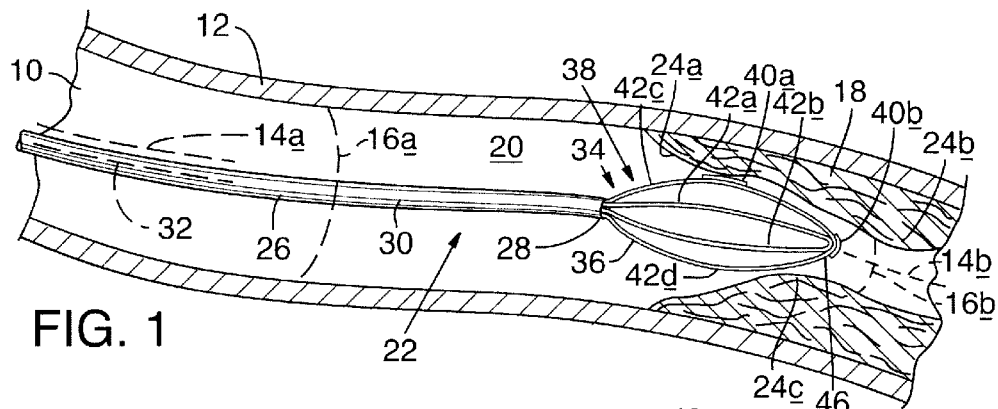
FIG. 1 is a isometric view from the side of the present invention showing a guidewire and a wire lead inserted through the guidewire, the wire lead including four wires at a distal portion extending beyond a distal end of the guidewire, the distal portion formed in an ovoid basket-shape with thermocouples disposed on one side and on a forward or distal tip of the four-wire basket-shape, the device shown inserted in a plaque-affected fluid passageway, the basket-shape having a maximum outer circumference smaller than a primary inner circumference of the passageway, except at an area of interest where the plaque has narrowed the circumference of the passageway.

As shown in FIG. 1, a fluid passageway, such as artery 10, is formed of a wall 12 having a generally cylindrical shape and defining a central longitudinal axis 14a and an inner circumference 16a. The position of the axis and the size of the inner circumference vary over the length of artery 10, shifting and narrowing in locations, as shown for axis 14b and inner circumference 16b, where a buildup or a growth 18 of arteriosclerotic plaque has developed on an internal surface 20 of wall 12. Under normal conditions blood is flowing under varying pressure through artery 10.

One factor believed to indicate the presence of the unstable plaque of acute coronary heart disease is an increased temperature measurable at the surface of the plaque. Elevated levels of inflammatory cells are believed to cause the increased temperature. A device indicated generally at 22 for measuring temperature along interior surface 20, including at one or more areas of interest, such as those indicated at 24a, 24b, and 24c, where plaque 18 is located, includes a guidewire 26 configured for insertion into artery 10 and sliding movement along the passageway under the control of a physician.

Guidewire 26 is preferably a stainless steel, hollow tube, including an open proximal end (not shown), an open distal end 28, and a generally cylindrical outer surface 30 extending between the ends. The guidewire defines a central longitudinal axis 32. The outer diameter of the guidewire is preferably about 0.014-inches and is typically constant throughout the length of the guidewire. It will be understood that guidewire 26 is provided with a lateral flexibility sufficient for sliding movement through the turns typical for human passageways, but rigid enough that, even at a length of four feet or more, a translational force applied adjacent the proximal end is transmitted to the distal end for sliding motion along the passageway, and that a torsional force applied adjacent the proximal end is likewise transmitted to the distal end to turn the distal end to aid in steering the guidewire.

Figure 4:
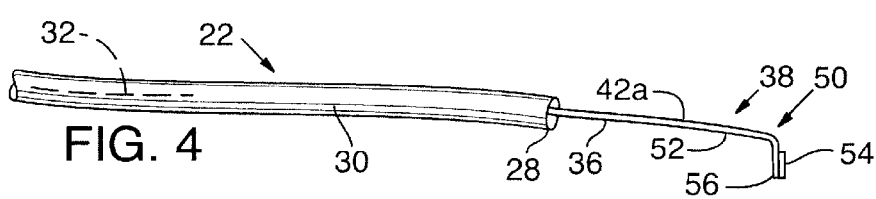
FIG. 4 is an isometric view of another embodiment of the present invention, including a guidewire, and a wire lead inserted therethrough with a distal portion of the wire lead extending beyond a distal end of the guidewire, the distal portion terminating in an L-shape with a thermocouple disposed at the tip of the L.
Figure 5:
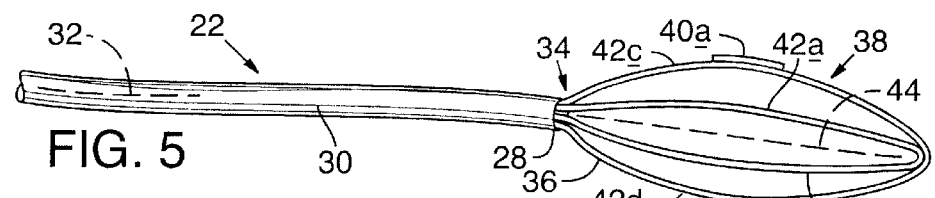
FIG. 5 is an isometric view of an embodiment of the present invention, similar to the embodiment in FIG. 1, but with a thermocouple only along a side of the basket-shape.
Figure 6:
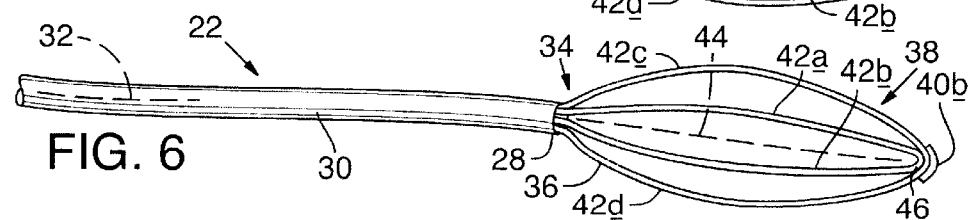
FIG. 6 is an isometric view of an embodiment of the present invention, similar to the embodiment in FIG. 1, but with a thermocouple only at a forward or distal end or tip of the basket-shape.

Guidewire 26 has an inner diameter sufficient to accommodate a wire lead, indicated generally at 34, which is inserted through guidewire 26. Wire lead 34 may be held in place in guidewire 26 by a frictional fit, or adhesively fixed in place. Wire lead 34 can be provided in a variety of different shapes for accurate measurement of temperature under various conditions within the passageway. Wire lead 34 is preferably made of one or more flexible, resilient metal wires 36 designed for medical applications, such as Nitinol® or constantan. Wires 36 are sized for insertion through the guidewire, e.g., as shown in FIGS. 1, 5, and 6, where four wires 36 extend through the guidewire and have an outer diameter of typically about 0.003-inches. In embodiments shown in FIGS. 2 and 3, with two wires 36 extending through guidewire 26, wires 36 are typically about 0.005-inches, and a single wire 36, as shown in FIG. 4, typically is about 0.010-inches in outer diameter. Wires 36 typically extend all the way through guidewire 26, and have proximal ends (not shown) extending beyond the proximal end of guidewire 26, which are configured for connection to a temperature monitor (not shown).

Wire lead 34 is typically inserted into guidewire 26 with a distal portion 38 of wire lead 34 that extends beyond distal end 28 of guidewire 26. If a frictional fit is used for one or more of wires 36, such wires may be moved longitudinally relative to guidewire 26 to vary the length, circumference and shape of distal portion 38.

One or more thermocouples 40a, 40b are disposed on distal portion 38 of wire lead 34, and wires 36 at distal portion 38 are formed in a shape for flexible, resilient positioning of the thermocouples within the passageway. In the embodiment shown in FIGS. 1, 5, and 6, four lengths 42a–d of wire 36 at distal portion 38 are disposed in a looped, ovoid or basket shape, each of wire lengths 42a–d providing a side of the looped, basket shape, and the sides are generally spaced apart at about 90-degree intervals. This embodiment will also be understood to include a first looped shape formed by wire lengths 42a and 42b and a second looped shape formed by wire lengths 42c and 42d wherein the second looped shape is roughly orthogonal to the first looped shape. As shown in FIGS. 5 and 6, wire lead 34 defines a central longitudinal axis 44. Wire lengths 42a–d are flexible and resilient to conform generally to inner circumference 16a, 16b of artery 10 and to position wire lead 34 with its central axis 44 generally coincident with central axis 14a, 14b of artery 10 as wire lead 34 is moved through artery 10. Wire lengths 42a–d may be rigidly fixed together at tip 46.

As shown in FIG. 1, a first thermocouple 40a is positioned on the side of the looped shape of distal portion 38 provided by wire length 42c at a position, typically at a maximum outer circumference of distal portion 38, that is adjacent distal end 28 of guidewire 26 and nominally radially outside of the outer diameter at distal end 28 of guidewire 26. Wire lead 34 is thus configured to bring thermocouple 40a to an area of interest where a temperature measurement is desired within artery 10, such as at plaque inner surfaces 24a, 24b, 24c. Distal portion 38 of wire lead 34, being flexible and resilient, biases thermocouple 40a in a radially outward direction from central axis 44 of wire lead 34 and into contact with the areas of interest 24a, 24b, 24c on inner surface 20 of artery 10 for accurate measurement of the temperature there. Wire lead 34 flexes in response to contact with the interior surface of artery 10 and allows thermocouple 40a to move radially inward from its nominal position.

Thermocouples 40a, 40b are preferably capable of calibration to 0.05-degrees C., so that the thermocouples can sense the temperature remotely within artery 10 and register the temperature on the external temperature monitor so that accurate measurement can be performed.

Guidewire 26 is primarily provided to give sufficient longitudinal and torsional stiffness to device 22, but alternatively guidewire 26 may provide a conductive path between the thermocouple and the temperature monitor for measurement of temperature, or wire lead 34 may be constructed with a portion providing sufficient structural strength, thus incorporating the function of guidewire 26.

The second thermocouple 40b shown in FIG. 1 is positioned at a forward or distal tip 46 of distal portion 38 of wire lead 34, and thus thermocouple 40b may be brought into contact with an area of interest where plaque 18 has completely, or almost completely occluded artery 10 to an extent that wire lead 34 cannot be further inserted. Thermocouple 40b at tip 46 is also useful for measuring the temperature within the blood flow rather than at interior surface 20.

Guidewire 26, wire lead 34, and thermocouple 40 may be constructed in the manner shown in Japanese patent application no. H11-249287, SN-3073999902, of Internova Corporation and Richard R. Heuser, filed on Sep. 2, 1999 and entitled Guidewire for Medical Application, which is hereby incorporated by reference. In that embodiment, guidewire 26 is a stainless steel mandrill having a lengthwise groove into which wire lead 34 is laid and affixed, e.g., by adhesives, and guidewire 26 is one of the conductors connected to the temperature monitor. Wire lead 34 is a single, insulated constantan wire providing the other conductive path to the temperature monitor. Thermocouple 40 is formed by soldering together the constantan wire and the stainless steel guidewire.

Figure 2:
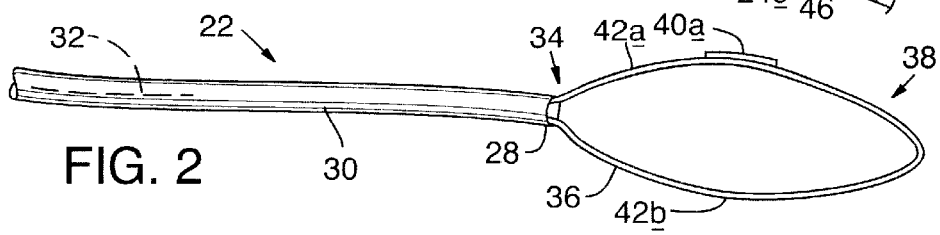
FIG. 2 is an isometric view of the guidewire, wire lead and thermocouple of the present invention, this embodiment including only two wires at a distal portion of the wire lead formed in an oval, looped shape with the thermocouple disposed on one side of the looped-shape.
Figure 3:
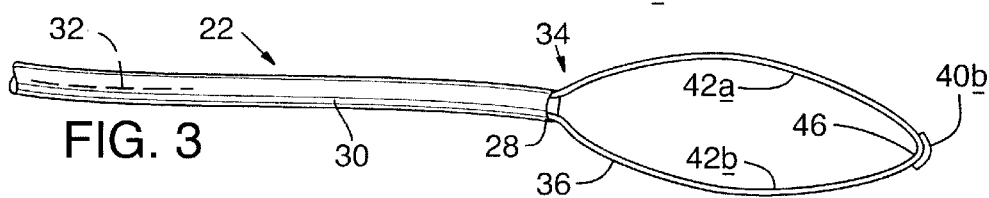
FIG. 3 is an isometric view of the guidewire, wire lead and thermocouple of the present invention, in another embodiment including only two wires at a distal portion of the wire lead formed in an oval, looped shape with the thermocouple disposed on a forward or distal tip of the looped shape.

In the embodiment of FIGS. 2 and 3, distal portion 38 includes a two-sided looped shape formed by two wire lengths 42a and 42b with a single thermocouple 40a(FIG. 2) or 40b (FIG. 3) disposed on a side or on tip 46, respectively, of distal portion 38. It will be understood that wire lead 34 and guidewire 26 as shown in FIGS. 2 and 3 have similar capabilities as the embodiment of FIGS. 1, 5, and 6 for slidable movement through artery 10 to bring thermocouple 40a to an area of interest within artery 10 at a position nominally radially outside of guidewire axis 32 for radially outwardly biased contact with interior surface 20 at the area of interest for accurate measurement of temperature there. Thermocouple 40b as shown in FIG. 3 operates the same as for the embodiment of FIG. 1 but is provided in a simpler structure for measurement of temperature in the blood stream or at the surface of total or near-total occlusion.

In the embodiment shown in FIG. 4 distal portion 38 of wire lead 34 is a single wire length 42a provided with an L-shape 50 at its terminal end 52, with thermocouple 54 disposed adjacent a tip 56 of L-shape 50. Thermocouple 54 in this embodiment is thus disposed adjacent distal end 28 of guidewire 26 at a position nominally radially outside of the outer diameter of guidewire 26 for biased contact with and measurement of the temperature of, interior surface 20 of artery 10. The L-shaped tip of this embodiment is also useful in maneuvering wire lead 34 by torsional force applied at the proximal end of guidewire 26, and thereby encouraging tip 56 to enter a desired arterial branch.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. No single feature, function, element or property of the disclosed embodiments is essential to all of the disclosed inventions. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also included within the subject matter of the inventions of the present disclosure.

I claim:

1. A device for sensing temperature remotely at an area of interest of an interior surface of a fluid passageway in a human body and registering the temperature on an external temperature monitor, the device comprising:

a wire lead configured for insertion into the passageway, the wire lead having sufficient lateral flexibility for sliding movement through the passageway;

a thermocouple disposed on the wire lead and configured to be connected to the temperature monitor;

wherein the wire lead is provided with sufficient longitudinal rigidity that a translational force applied to the wire lead is transmitted forward for sliding motion of the wire lead along the passageway to bring the thermocouple to the area of interest and the wire lead biases the thermocouple into contact with the area of interest of the interior surface of the fluid passageway.

2. The device of claim 1 wherein a distal portion of the wire lead is configured in a generally looped shape having two sides, and the thermocouple is disposed on one of the sides.

3. The device of claim 2 wherein the wire lead is further configured in the generally looped shape to have four sides, the four sides of the generally looped shape generally spaced apart at about 90-degree intervals.

4. The device of claim 1 wherein the wire lead places the thermocouple at a nominal position, and the wire lead is configured to allow the thermocouple to move radially inwardly from the nominal position.

5. The device of claim 4 wherein a distal portion of the wire lead is configured in a first looped shape and a second looped shape roughly orthogonal to the first looped shape.

6. A device for sensing temperature remotely at an area of interest of an interior surface of a fluid passageway in a human body and registering the temperature on an external temperature monitor, the device comprising:

a wire lead configured for insertion into the passageway, the wire lead defining a central longitudinal axis, the wire lead having sufficient lateral flexibility for sliding movement through the passageway;

a thermocouple disposed on the wire lead and configured to be connected to the temperature monitor;

wherein the wire lead is provided with sufficient longitudinal rigidity that a translational force applied to the wire lead is transmitted forward for sliding motion of the wire lead along the passageway to bring the thermocouple to the area of interest and the wire lead biases the thermocouple in a radially outward direction from the central axis for measurement of the temperature at the area of interest of the interior surface of the fluid passageway.

7. The device of claim 6 wherein the wire lead includes a distal portion having a looped shape with at least two sides, and the thermocouple is disposed on one of the sides.

8. The device of claim 6 further comprising a guidewire having a proximal end and a distal end, wherein the wire lead is substantially disposed within the guidewire, the guidewire providing the longitudinal rigidity for sliding motion of the wire lead along the passageway, the wire lead including a distal portion extending beyond the distal end of the guidewire, and wherein the thermocouple is disposed on the distal portion of the wire lead.

9. The device of claim 8 wherein the guidewire includes an outer surface defining at the distal end an outer diameter, and the distal portion of the wire lead positions the thermocouple radially outside of the outer diameter.

10. The device of claim 6 wherein the passageway defines a central longitudinal axis and wherein the wire lead is configured to maintain the wire lead's central axis generally coincident with the passageway's central axis as the wire lead is moved through portions of the passageway narrower than a nominal outer circumference of the wire lead.

11. A device for insertion into a passageway to sense temperature remotely within the passageway and register the temperature on an external temperature monitor, the device comprising:

a guidewire configured for insertion into the passageway and sliding movement along the passageway, the guidewire having sufficient lateral flexibility for movement through the passageway and sufficient longitudinal rigidity that a translational force applied to the guidewire is transmitted forward for sliding motion of the guidewire along the passageway, the guidewire having a proximal end and a distal end, and an outer surface extending between the ends, the outer surface defining at the distal end an outer diameter;

a wire lead coupled to the guidewire for movement along the passageway; and a thermocouple disposed adjacent the distal end of the guidewire and radially outside of the outer diameter of the guidewire, the thermocouple configured to be connected to the temperature monitor via the wire lead.

12. The device of claim 11 wherein the wire lead includes a distal portion that is capable of extending beyond the distal end of the guidewire.

13. The device of claim 12 wherein the thermocouple is disposed on the wire lead.

14. The device of claim 13 wherein the guidewire defines a central longitudinal axis, and the wire lead biases the thermocouple in a radially outward direction from the central axis.

15. The device of claim 12 wherein the distal portion of the wire lead is disposed in a looped shape having two sides, and wherein the thermocouple is disposed on one of the sides.

16. The device of claim 15 wherein the looped shape includes a tip, and further comprising a second thermocouple disposed on the tip.

17. The device of claim 15 wherein the looped shape of the wire lead biases the thermocouple radially outside of the outer diameter of the guidewire at a nominal position, and wherein the wire lead is flexible to allow the thermocouple to move radially inwardly from the nominal position.

18. The device of claim 11 wherein the wire lead includes a distal portion terminating in an L-shape, and the thermocouple is disposed on the tip of the L-shape.

19. The device of claim 11 wherein the thermocouple is biased to a nominal position radially outside of the outer diameter of the guidewire, and the thermocouple is capable of moving radially inward from the nominal position.

20. A device for sensing temperature remotely at an area of interest within a fluid passageway in a human body and registering the temperature on an external temperature monitor, the device comprising:

a wire lead configured for insertion into the passageway, the wire lead having sufficient lateral flexibility for sliding movement through the passageway, the wire lead including a distal portion formed in a looped shape;

a thermocouple disposed on the wire lead and configured to be connected to the temperature monitor;

wherein the wire lead is provided with sufficient longitudinal rigidity that a translational force applied to the wire lead is transmitted forward for sliding motion of the wire lead along the passageway to bring the thermocouple to the area of interest and the distal portion of the wire lead is formed of a resilient material that flexes when the thermocouple is brought into contact with the area of interest.

* * * * *